(12) United States Patent
Nelson

(10) Patent No.: US 8,222,432 B2
(45) Date of Patent: Jul. 17, 2012

(54) STABLE, WATER-INSOLUBLE R-(+)-α-LIPOIC ACID SALT USEFUL FOR THE TREATMENT OF DIABETES MELLITUS AND ITS CO-MORBIDITIES

(75) Inventor: Deanna J. Nelson, Raleigh, NC (US)

(73) Assignee: BioLink Life Sciences, Inc., Cary, NC (US)

( * ) Notice: Subject to any disclaimer, the term of this patent is extended or adjusted under 35 U.S.C. 154(b) by 0 days.

(21) Appl. No.: 13/125,724

(22) PCT Filed: Oct. 24, 2008

(86) PCT No.: PCT/US2008/081128
§ 371 (c)(1),
(2), (4) Date: May 11, 2011

(87) PCT Pub. No.: WO2010/047717
PCT Pub. Date: Apr. 29, 2010

(65) Prior Publication Data
US 2011/0213022 A1    Sep. 1, 2011

(51) Int. Cl.
C07D 339/02    (2006.01)
C07D 341/00    (2006.01)
C07D 409/00    (2006.01)
(52) U.S. Cl. ........................................................ 549/39
(58) Field of Classification Search ............... 549/39
See application file for complete search history.

(56) References Cited

U.S. PATENT DOCUMENTS

| | | | |
|---|---|---|---|
| 5,728,735 A | 3/1998 | Ulrich et al. | |
| 6,288,106 B1 * | 9/2001 | Pearson et al. | 514/440 |
| 6,524,619 B2 * | 2/2003 | Pearson et al. | 424/472 |
| 6,670,484 B2 | 12/2003 | Villani et al. | |
| 6,689,385 B2 | 2/2004 | Richardson et al. | |
| 6,864,374 B2 | 3/2005 | Villani et al. | |
| 7,060,295 B2 * | 6/2006 | Richardson et al. | 424/464 |
| 8,080,674 B2 * | 12/2011 | Chiu | 549/22 |
| 2004/0044046 A1 | 3/2004 | Ames | |
| 2010/0009948 A1 * | 1/2010 | Nelson et al. | 514/167 |

OTHER PUBLICATIONS

Carlson et al. (Alternative Medicine Review, vol. 12, Issue 4 (2007): p. 343-351.*
Shay KP, Moreau RF, Smith EJ, Smith AR, Hagen RM. Alpha-lipoic acid as a dietary supplement: Molecular mechanisms and therapeutic potential. Biochim Biophy Acta Oct. 2009; 1790(10): 1149-1160.

* cited by examiner

*Primary Examiner* — Yong Chu
*Assistant Examiner* — Valerie Rodriguez-Garcia
(74) *Attorney, Agent, or Firm* — Casimir Jones SC

(57) ABSTRACT

The present invention relates to oral nutritional and therapeutic products which are useful for preventing or treating compensated and decompensated insulin resistance and associated diseases and sequelae, or diabetes mellitus and its sequelae, complications, and co-morbidities, comprising magnesium R-(+)-alpha-lipoate.

1 Claim, 2 Drawing Sheets

STABLE, WATER-INSOLUBLE R-(+)-α-LIPOIC ACID SALT USEFUL FOR THE TREATMENT OF DIABETES MELLITUS AND ITS CO-MORBIDITIES

CROSS-REFERENCE TO RELATED APPLICATION

The present application is a national phase application under 35 U.S.C. §371 of pending International Patent Application No. PCT/US2008/081128, filed on Oct. 24, 2008, which published on Apr. 29, 2010 as Publication No. WO 2010/047717, which is herein incorporated by reference in its entirety.

FIELD OF THE INVENTION

The present invention relates to oral nutritional and therapeutic products which are useful for preventing or treating compensated and decompensated insulin resistance and associated diseases and sequelae, or diabetes mellitus and its sequelae, complications, and co-morbidities. The pharmaceutical products and methods of the present invention are particularly useful in preventing or treating diabetes mellitus and its sequelae, complications, and co-morbidities in humans.

BACKGROUND OF THE INVENTION

Diabetes mellitus (commonly referred to as "diabetes") is a syndrome of disordered metabolism resulting in abnormally high blood sugar levels. Type 2 diabetes mellitus (non-insulin dependent diabetes mellitus) is the most common form of diabetes and affects 17 million people in the U.S. Late diagnosis, coupled with poor disease management, can result in long-term complications such as microvascular damage and diseases of the eye, nervous system, and kidney. These complications lead to cataracts and blindness, nerve damage (neuropathy), kidney failure, cardiovascular disease, and death.

The Diabetes Control and Complications trial demonstrated over 5 years of follow-up study that tight control of blood glucose is effective in reducing clinical complications significantly. However, trial data showed that even optimal control of blood glucose could not prevent complications of the disease.

It is known that oxidative stress is causally related to the progression of diabetes and sequelae, co-morbidities, and complications of the disease. Oxidative stress is defined in general as excess formation and/or insufficient removal of highly reactive inflammatory species such as reactive oxygen species (ROS; including, by way of example, superoxide radical anion, hydroxyl radical, peroxyl radicals, hydroperoxyl radicals, hydrogen peroxide, and hypochlorous acid) and reactive nitrogen species (RNS; including, by way of example, nitric oxide, nitrogen dioxide, peroxynitrite, nitrous oxide, and alkyl peroxynitrates). Both ROS and RNS are generated under physiological conditions; many of these species have physiological activity as signaling molecules and defense mechanisms. However, excess generation of these reactive species, particularly when the excess continues over time, causes damage to proteins, lipids, and DNA.

Direct evidence of oxidative stress in diabetes is based on studies in which markers of oxidative stress, such as plasma and urinary F2-isoprostane, plasma and tissue levels of nitrotyrosine and superoxide radical anion, and imbalances in physiological anti-oxidants, were measured. In diabetes, these markers are generated via non-enzymatic, enzymatic and mitochondrial pathways.

Since anti-oxidants are known to abrogate oxidative stress, a number of clinical trials have evaluated the beneficial effects of anti-oxidants such as vitamin C, vitamin E, and α-lipoic acid on the course of diabetes, its sequelae, and co-morbidities. To date, only the results from clinical studies with α-lipoic acid have supported its clinical use as a treatment for diabetes and its co-morbidities. For example, in the Alpha Lipoic Acid in Diabetic Neuropathy (ALADIN) study, administration of α-lipoic acid (>600 mg/day) significantly improved patient symptoms. The ALADIN II Study demonstrated that long-term (24 months) use of α-lipoic acid (600 or 1200 mg daily) improved nerve function. ALADIN III, a randomized multicenter double-blind placebo controlled study, showed that in a cohort of 509 patients, 600 mg α-lipoic acid administered daily for 6 months improved neuropathy impairment score as early as 19 days, which was maintained up to 7 months. The DEKAN (Deutsche kardiale autonome neurpathie) study evaluated the effect of 800 mg α-lipoic acid or placebo daily in diabetic patients with cardiac autonomic neuropathy for 4 months and showed that heart rate variability, an indicator of cardiac autonomic neuropathy, significantly improved with α-lipoic acid treatment. The SYDNEY trial investigated the effect of α-lipoic acid treatment on sensory symptoms of diabetic polyneuropathy as assessed by the Total Symptom Score. Administration of α-lipoic acid over a 3-week period improved sensory symptoms such as pain, prickling, and numbness. A recent meta-analysis of clinical trials with α-lipoic acid concluded that treatment with α-lipoic acid (600 mg/day) over a 3-week period is safe and effective in improving positive neuropathic symptoms as well as neuropathic deficits. [J. S. Johansen, A. K. Harris, D. J. Rychly, and A. Ergul, "Oxidative stress and the use of antioxidants in diabetes: Linking basic science to clinical practice," Cardiovasc Diabetol 2005; 4:5, and references therein]

α-Lipoic acid is the common name for the chiral compound 1,2-dithiocyclopentane-3-valeric acid. α-Lipoic acid is available commercially as both the racemic mixture, RS-α-lipoic acid (also commonly known as thioctic acid), and as the single enantiomer, R-(+)-α-lipoic acid. All of the clinical studies presented above used RS-α-lipoic acid.

R-(+)-α-lipoic acid is the form of α-lipoic acid found in the body. Lysine-bound R-(+)-α-lipoate is a coenzyme of α-ketoacid dehydrogenases (pyruvate dehydrogenase, α-ketoglutarate dehydrogenase, etc.) and acts at a key site in the sugar and energy metabolism of the cell. In addition, R-(+)-α-lipoate functions as a physiological redox system and is reduced intracellularly to its corresponding R-(+)-α-dihydrolipoate, which is subsequently re-oxidized, both intra- and extra-cellularly, to R-(+)-α-lipoate. Dihydrolipoate is able to regenerate other anti-oxidants such as vitamin C, vitamin E, and reduced glutathione through redox cycling.

It is well known that the pharmacological properties of the two enantiomers of α-lipoic acid differ with respect to their physiological activities. By way of example, U.S. Pat. Nos. 5,693,664, 5,948,810, 6,284,787, and U.S. Patent Application Publication No. US 2008/0095741 (all to Wessel et al.) disclose that R-(+)-α-lipoic acid, its water-soluble salts, its esters, and its amides are more suitable for the prevention and treatment of diabetes and its complications than are the enantiomeric S-(−)-α-lipoic acid, its water-soluble salts, its esters, and its amides. (The water-soluble salts disclosed by Wessel include salts of organic amines, such as α-methylbenzylamine, diphenylamine, trometamol, and 2-amino-2-hydroxymethyl-1,3-propylene glycol.) For example, glucose assimilation was stimulated by the R-enantiomer of lipoic acid by a factor greater than 2, comparable to the effect of 200 nM insulin, whereas the S-enantiomer effected little or no change. Likewise, R-(+)-α-lipoate stimulated the translocation of glucose transporters (GLUT 1 and GLUT 4) from the cytosol to the plasma membrane; S-(−)-α-lipoate had no effect or has an inhibiting effect and appeared to lower the total content of glucose transporters. Further, the activity of a key enzyme involved in glucose metabolism, pyruvate dehydrogenase, was increased by R-(+)-α-lipoate but inhibited by S-(−)-α-lipoate.

It is also known that RS-α-lipoic acid is more stable than R-(+)-α-lipoic acid. RS-α-Lipoic acid may be stored in a closed and sealed amber container at room temperature for a year or longer. In contrast, R-(+)-α-lipoic acid must be stored in a closed and sealed amber container at refrigerated temperatures and must be used within a few months, since it gradually polymerizes to intractable polymers and degrades to physiologically and therapeutically inactive compounds by loss of sulfur-containing compounds.

Further, it is known that adequate magnesium is essential for glycolysis, formation of adenosine-3",5"-cyclic monophosphate, energy-dependent membrane transport, and over 300 other enzyme processes. Magnesium plays the role of a second messenger for insulin action. Conditions associated with insulin resistance (i.e., reduced sensitivity to the activity of insulin), such as diabetes, hypertension or aging, are also associated with low intracellular magnesium contents. In diabetes mellitus, low intracellular magnesium levels have been reported, likely as a result from both increased urinary losses and insulin resistance. Chronic magnesium supplementation can contribute to an improvement in both islet beta-cell response and insulin action in non-insulin-dependent diabetic subjects.

Therefore, a significant, unmet need exists for provision of a stable drug for preventing or treating diabetes mellitus and sequelae, complications, and co-morbidities. If that stable drug contained magnesium, the properties of magnesium disclosed above indicate that the stable, magnesium-containing drug would provide additive therapeutic benefits to those suffering from metabolic disorders related to disordered glycolysis. The present invention addresses this unmet need by providing a stable magnesium-containing drug.

SUMMARY OF THE INVENTION

The present invention is an oral nutritional and therapeutic composition useful for preventing or treating diabetes mellitus and its sequelae, complications, and co-morbidities, comprising a unit dosage or serving of magnesium R-(+)-alpha-lipoate. A method of preventing or treating diabetes mellitus, its sequelae, complications, and co-morbidities in a human, comprising administering to said human a safe and effective amount of a supplement comprising magnesium R-(+)-alpha-lipoate, is also disclosed. Further, a method of preventing and treating diabetes mellitus, its sequelae, complications, and co-morbidities in a warm-blooded animal with a therapeutically effective amount of a pharmaceutical composition comprising magnesium R-(+)-alpha-lipoate is disclosed. A method of preparing magnesium R-(+)-alpha-lipoate is also provided. In some embodiments, the present invention comprises use of magnesium R-(+)-alpha-lipoate in the manufacture of a medicament for the prevention or treatment of compensated and decompensated insulin resistance and associated diseases and sequelae, or diabetes mellitus and its sequelae, complications, and co-morbidities.

Other features, advantages, and embodiments of the invention will be apparent to those of ordinary skill in the art from the following description, examples, and appended claims.

DETAILED DESCRIPTION OF THE INVENTION

Figure 1:
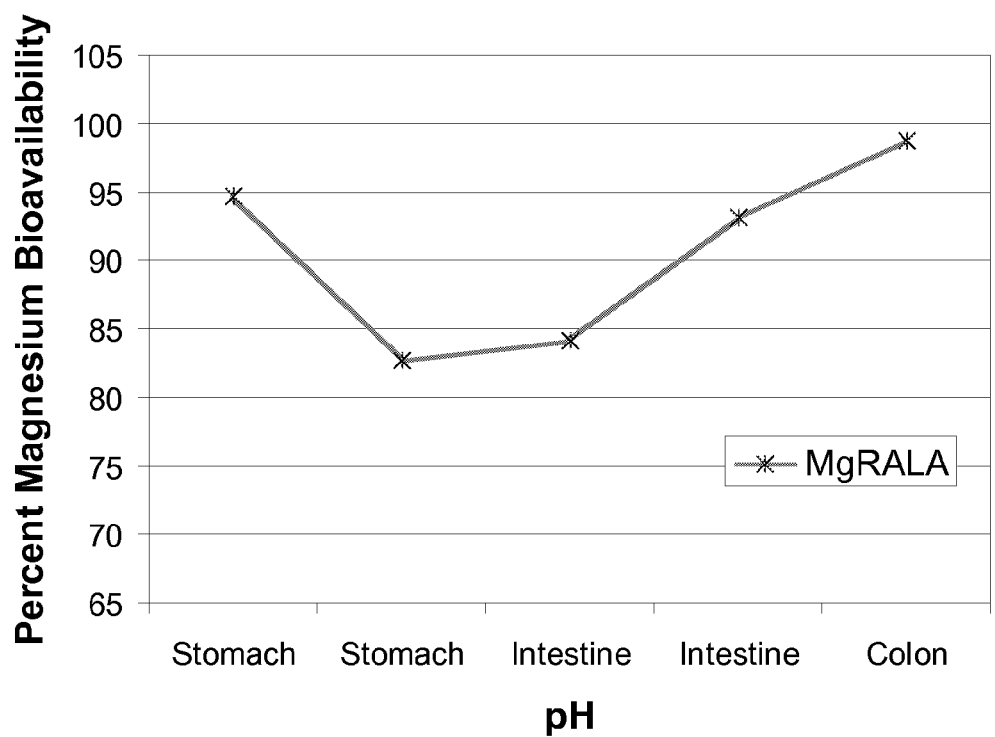
FIG. 1 is a graph showing the percentage of bioavailable magnesium in magnesium R-(+)-alpha-lipoate (Mg RALA) at each value of pH in the range from pH 4 to pH 8, the pH range of the human gastrointestinal tract.
Figure 2:
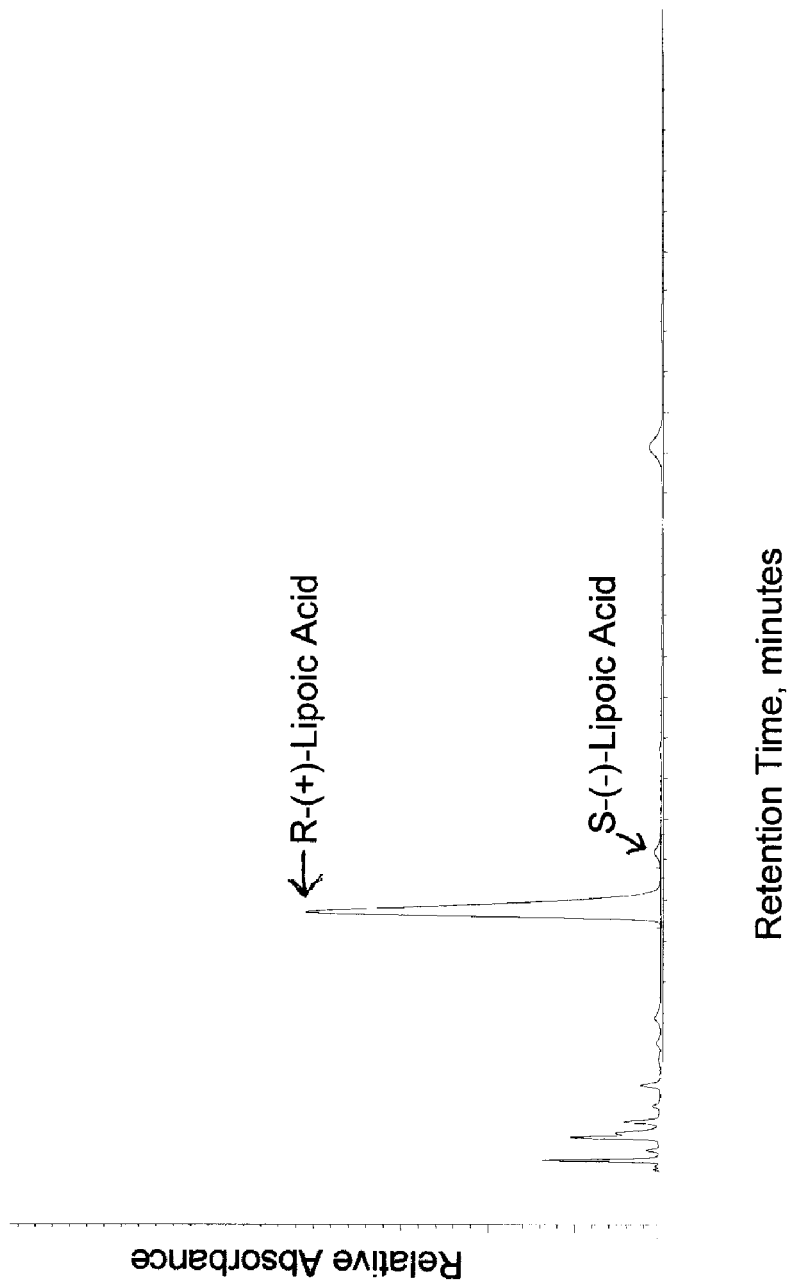
FIG. 2 is a chromatogram showing the relative retention times of R-(+)-alpha-lipoate of the invention and S-(−)-alpha-lipoate. The relative peak heights confirm that R-(+)-alpha-lipoate of the invention has at least 95% chiral purity.

The present invention is an oral nutritional and therapeutic composition useful for the treatment of diabetes mellitus and its sequelae, co-morbidities, and complications, comprising a unit dosage or serving of magnesium R-(+)-alpha-lipoate. This agent promotes the assimilation of blood sugar in the tissue. This activity is of clinical relevance in the case of pathological disorders of the control of blood sugar adjustment, as in the case of diabetes mellitus types I and II, or in the case of disorders in insulin sensitivity of the tissue (insulin resistance). This applies in the case of monotherapy, as well as in the case of a combination with other drugs for the treatment of diabetes mellitus or of insulin resistance, such as oral anti-diabetic drugs and, in particular, insulin. Furthermore, complications, sequelae, or co-morbidities of diabetes mellitus or of insulin resistance can also be affected therapeutically by the treatment of the basic diseases with the stable drug of this invention. The composition is useful in men and women.

The present invention also relates to a method of treating compensated and decompensated insulin resistance and, with that, of associated diseases and sequelae, or of diabetes mellitus and its sequelae and complications in a human, comprising administering to said human a safe and effective amount of a supplement comprising an effective amount of magnesium R-(+)-alpha-lipoate.

In addition, the present invention relates to a method of preventing and treating compensated and decompensated insulin resistance and, with that, of associated diseases and sequelae, or of diabetes mellitus and its sequelae and complications in a warm-blooded animal with a therapeutically effective amount of a pharmaceutical composition comprising pharmaceutical quality magnesium R-(+)-alpha-lipoate. Included within the scope of this invention is a method of preventing and treating compensated and decompensated insulin resistance and, with that, of associated diseases and sequelae, or of diabetes mellitus and its sequelae and complications in a warm-blooded animal using oral pharmaceutical compositions comprising pharmaceutical quality magnesium R-(+)-alpha-lipoate and a suitable pharmaceutical carrier.

Magnesium R-(+)-alpha-lipoate is the magnesium salt of R-(+)-α-lipoic acid. Magnesium R-(+)-α-lipoate is a stable, non-hygroscopic, light yellow powder having a molecular formula of $Mg(C_8H_{13}O_2S_2)_2$, the general formula

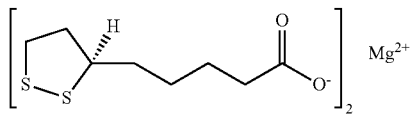

and a molecular weight of 434.94. Pharmaceutical quality magnesium R-(+)-alpha-lipoate of this invention has at least about 95% chiral purity. In other words, pharmaceutical quality magnesium R-(+)-alpha-lipoate of the invention contains less than about 5% of magnesium S-(−)-alpha-lipoate.

Magnesium R-(+)-α-lipoate has been selected because this stable salt provides both magnesium and R-(+)-alpha-lipoate, the anion of R-(+)-alpha-lipoic acid. R-(+)-α-Lipoate is the form of alpha-lipoic acid naturally found in the human body. Further, R-(+)-alpha-lipoate is a widely distributed physiological antioxidant that combines free radical scavenging properties with an ability, after intracellular reduction to dihydrolipoic acid, to regenerate the levels of other nonenzymatic and enzymatic antioxidants, including glutathione (GSH), ascorbate, α-tocopherol, catalase and GSH peroxidase. The physiological form of R-(+)-α-lipoate, the R-(+)-enantiomer, is present in all eukaryotic and prokaryotic cells. R-(+)-α-Lipoate has demonstrated safety and an absence of toxicity when administered chronically to humans. Magnesium is the fourth most prevalent element in the body and the second most abundant intracellular ion. Since magnesium is a cofactor in over 300 enzyme systems, adequate magnesium is essential for many biosynthetic processes, including, by way of example, glycolysis, formation of adenosine-3",5"-cyclic monophosphate, energy-dependent membrane transport, and transmission of the genetic code. The relationship between insulin and magnesium has been recently studied by Paolisso et al. [G. Paolisso, A. Scheen, F. D'Onofrio, and P. Lefebvre, Magnesium and glucose homeostasis. Diabetologia 1990; 33(9): 511-514.] These studies showed that magnesium plays the role of a second messenger for insulin action. Conversely, insulin itself was shown to be an important regulatory factor of intracellular magnesium accumulation. The authors reported that conditions associated with insulin resistance, such as hypertension or aging, are also associated with low intracellular magnesium contents. In diabetes mellitus, low intracellular magnesium levels have been reported, likely as a result from both increased urinary losses and insulin resistance. The extent to which such a low intracellular magnesium content contributes to the development of macro- and microangiopathy co-morbidities of diabetes remains to be established. A reduced intracellular magnesium content has been reported to contribute to the impaired insulin response and action which occurs in Type 2 (non-insulin-dependent) diabetes mellitus. Chronic magnesium supplementation contributes to an improvement in both islet beta-cell response and insulin action in non-insulin-dependent diabetic subjects.

In general, compensated insulin resistance implies long-standing and adequate control of blood glucose levels as manifested by glycosylated hemoglobin (HbA1c) levels (a simple and routine blood test) within normal levels, i.e., <about 7.0%. This is an index of metabolic control over several months that doctors use as an index of how well a patient is balancing diet, medications (insulin, etc.), exercise and other variables, i.e., how well "compensated" they are with their diabetes.) Poorly compensated insulin resistance (levels of Hb1Ac higher than about 7.0%) is associated with retinopathy, nephropathy, neuropathy, vasculopathy, etc.

The term "bioavailability" refers to the amount of a substance that is absorbed in the intestines and ultimately available for biological activity in a subject's cells and tissues.

The term "excipient material" is intended to mean any compound forming a part of the formulation which is not intended to have biological activity itself and which is added to a formulation to provide specific characteristics to the dosage form, including by way of example, providing protection to the active ingredient from chemical degradation, facilitating release of a tablet or caplet from equipment in which it is formed, and so forth.

By the terms "treating" and "treatment" and the like are used herein to generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein encompasses any treatment of a disease in a mammal, particularly a human and includes: (a) preventing the disease from occurring in a subject which may be predisposed to the disease but has not yet been diagnosed as having it; (b) inhibiting the disease or arresting its development; (c) relieving the disease, causing regression of the disease and/or its symptoms or conditions; or (d) returning a clinical value to the concentration range normally found in a subject.

The phrase "pharmaceutical quality" means that magnesium R-(+)-alpha-lipoate has a purity of at least about 90% and a chiral purity of at least about 90%. In addition, magnesium R-(+)-alpha-lipoate contains at most low part per million quantities of contaminating metals having known toxicities in humans. Examples of such metals include aluminum, lead, thallium, arsenic, barium, cadmium, and so forth.

The phrase "therapeutically effective" is intended to qualify the amount of magnesium R-(+)-alpha-lipoate for use in the orally administered composition of this invention which will achieve the goal of providing the quantity of R-(+)-alpha-lipoate and magnesium that are needed to prevent and treat compensated and decompensated insulin resistance and, with that, of associated diseases and sequelae, or of diabetes mellitus and its sequelae and complications in a warm-blooded animal.

For the purpose of this disclosure, a warm-blooded animal is a member of the animal kingdom which includes but is not limited to mammals and birds. The most preferred mammal of this invention is human.

To provide a more concise description, some of the quantitative expressions given herein are not qualified with the term "about." It is understood that whether the term "about" is used explicitly or not, every quantity give herein is meant to refer to the actual given value, and it is also meant to refer to the approximation to such given value that would reasonably be inferred based on the ordinary skill in the art, including approximations due to the experimental and/or measurement conditions for such given value.

Magnesium R-(+)-alpha-lipoate is not commercially available. In order to obtain sufficient quantities of this salt for use in this invention, a method of preparing pharmaceutical quality magnesium R-(+)-alpha-lipoate was required.

A method of preparing magnesium alpha-lipoate was disclosed by Pearson and Richardson in U.S. Pat. No. 6,288,106 B1. By this method, Pearson and Richardson disclose that a solution of alpha-lipoic acid in anhydrous ethanol was added with stirring to a solution of magnesium ethoxide in anhydrous ethanol. After stirring the reaction mixture for 30 minutes, the solvent was evaporated under reduced pressure to afford the magnesium salt of alpha-lipoic acid. Attempts to prepare pharmaceutical quality magnesium R-(+)-alpha-lipoate by the method of Pearson and Richardson failed. After evaporation of the solvents, as required by the method of Pearson and Richardson, a stringy, intractable polymer was obtained; no pharmaceutical quality magnesium R-(+)-alpha-lipoate was isolated.

R-(+)-α-Lipoic acid is a hydrophobic fatty acid that is known to undergo self-polymerization by heat- or light-induced cleavage of the sulfur-sulfur bond on one molecule to an unstable diradical that can interact with a second lipoic acid molecule at its sulfur-sulfur bond to generate a new ring-opened dimer of lipoic acid. This polymerization process can be repeated multiple times to generate polylipoates (i.e., polymers of ring-opened lipoic acid) of varying sizes and molecular weights. Monomeric R-(+)-alpha-lipoic acid is a yellow powder which is soluble in organic solvents such as alcohols, alkanes, etc. In contrast, the polylipoates are intractable, "gummy" yellow solids which adhere to the surfaces of containers and are essentially insoluble in aqueous or organic solvents.

Therefore, a synthesis of pharmaceutical quality magnesium R-(+)-alpha-lipoate was required which provided a powdery solid at room temperature without a requirement for evaporation of solvents or lengthy exposure to heating, wherein the solid had a purity of at least about 90% and a chiral purity of at least about 90% and within ±5% of the chiral purity of the R-(+)-alpha-lipoic acid starting material used for its preparation. R-(+)-alpha-Lipoic acid is an acid; a magnesium salt of an acid is obtained by reaction of the acid with a magnesium-containing base. To meet the additional criterion that the chiral purity of the magnesium R-(+)-alpha-lipoate equals the chiral purity of the R-(+)-alpha-lipoic acid starting material used for its preparation, the acid-base reaction must occur under conditions which are non-racemizing.

Magnesium hydroxide and magnesium oxide are commercially available bases containing magnesium. Both of these bases are insoluble in water or organic solvents. Because of this lack of solubility, reaction of magnesium hydroxide or magnesium oxide with R-(+)-alpha-lipoic acid does not occur under commercially useful conditions.

Magnesium methoxide, magnesium ethoxide, magnesium t-butoxide, and magnesium acetylacetonate are bases containing magnesium. A solution of magnesium methoxide in methanol is commercially available. A solution of magnesium ethoxide in ethanol can be prepared if 70 mL or more of ethanol per gram of magnesium ethoxide is heated. The inventors discovered that solutions of magnesium t-butoxide or magnesium acetylacetonate can be prepared in methanol or acetonitrile at room temperature.

Lipoic acid in solution is known to be susceptible to undesirable oxidation reactions. R-(+)-alpha-Lipoic acid in solution is very susceptible to oxidation by oxygen in air, particularly in the presence of a base. The inventors discovered that oxidation is prevented by preparing solutions of R-(+)-alpha-Lipoic acid in an inert atmosphere of nitrogen or argon and completing subsequent reactions under these conditions.

The inventors studied the reaction of 2 mole equivalents of R-(+)-alpha-lipoic acid with one mole equivalent of magnesium as a magnesium alkoxide. All reactions were carried out under an inert atmosphere and in subdued light, since these conditions prevented undesirable oxidation and/or polymerization. When a solution of magnesium ethoxide in ethanol was added to a solution of R-(+)-alpha-lipoic acid in ethanol, the volumes of ethanol that were required to obtain a solution of magnesium ethoxide at room temperature were too large to be commercially practical and the desired product, magnesium R-(+)-alpha-lipoate, failed to precipitate from solution. When a solution of magnesium ethoxide in methanol was added to a solution of R-(+)-alpha-lipoic acid in methanol or ethanol, the desired product, magnesium R-(+)-alpha-lipoate failed to precipitate from solution. When a solution of magnesium methoxide in methanol was added to a solution of R-(+)-alpha-lipoic acid in methanol or ethanol, the desired product, magnesium R-(+)-alpha-lipoate failed to precipitate from solution. If acetone was then added to induce precipitation, a glassy green solid was obtained that was not magnesium R-(+)-alpha-lipoate.

When a solution of magnesium acetylacetonate in methanol was added to a solution of R-(+)-alpha-lipoic acid in isopropanol, acetonitrile, or methanol/isopropanol, the desired product, magnesium R-(+)-alpha-lipoate was not obtained. Instead, a mixed salt, magnesium (R-(+)-alpha-lipoate)(acetylacetonate), was obtained.

After lengthy experimentation, the inventors discovered conditions for the preparation of magnesium R-(+)-alpha-lipoate, a powdery yellow solid. When a solution of magnesium methoxide in methanol was added to a solution of R-(+)-alpha-lipoic acid in isopropanol, acetonitrile, or methanol/isopropanol, the desired product, magnesium R-(+)-alpha-lipoate was obtained. Likewise, when a solution of magnesium t-butoxide in methanol was added to a solution of R-(+)-alpha-lipoic acid in isopropanol, acetonitrile, or methanol/isopropanol, the desired product, magnesium R-(+)-alpha-lipoate was obtained, but the yield was lower.

Under optimal conditions, the inventors discovered that the dropwise addition of a solution of magnesium methoxide in methanol to a clear solution of R-(+)-alpha-lipoic acid in methanol-isopropyl alcohol solution maintained under an inert atmosphere of nitrogen or argon and shielded from light provided magnesium R-(+)-alpha-lipoate as a solid, pale yellow precipitate. The volume ratios of solvent that were used in this preparation were from 25-35 milliliters isopropyl alcohol for each gram of R-(+)-alpha-lipoic acid and from 5-15 milliliters methanol for each gram of R-(+)-alpha-lipoic acid. (The volume of methanol that was used was provided by the magnesium methoxide solution and by supplemental methanol.) Magnesium R-(+)-α-lipoate was isolated by filtration and purified from contaminants by washing with fresh isopropyl alcohol. Magnesium R-(+)-α-lipoate did not melt at temperatures below 300° C. Analysis for magnesium content by titration showed that the magnesium content was about 5.6% by weight, as expected. Analysis for R-(+)-α-lipoate content by HPLC showed that the R-(+)-α-lipoate was about 95% by weight, as expected. HPLC analysis also confirmed that the chiral purity was greater than 95%, within ±5% of the 96% chiral purity of the R-(+)-alpha-lipoic acid starting material used for its preparation, an observation that confirmed that no racemization occurred during reaction. Analysis of trace metals by inductively coupled plasma mass spectrometry showed that magnesium R-(+)-α-lipoate contained only very low parts per million levels of toxic metals, such as aluminum, tin, arsenic, barium, lead, and thallium. Thus, this newly discovered method of preparing pharmaceutical quality magnesium R-(+)-α-lipoate uses inexpensive, commercially available reagents, reaction conditions that are easily scaled to commercial quantities, comprises reaction conditions that are non-racemizing, and provides greater than 65% yields of magnesium R-(+)-α-lipoate of greater than 95% purity and greater than 95% chiral purity.

Pharmaceutical quality magnesium R-(+)-α-lipoate that is prepared in the manner disclosed above is a stable magnesium salt of R-(+)-α-lipoic acid. We studied the stability of magnesium R-(+)-α-lipoate of the present invention during storage at ambient temperatures for a period of two years and found that the physical state and chemical properties of the salt did not change over time. The salt was not hygroscopic. This pale yellow salt had no characteristic odor or taste.

Magnesium R-(+)-alpha-lipoate is insoluble in water, a property that conventionally indicates that this salt has poor bioavailability. However, the inventor has found that both magnesium and R-(+)-α-lipoate ions are available from suspensions of the salt in aqueous solutions having a pH in the range from about 4 to about 8. This is the pH range that is found in parts of the human gastrointestinal system, where a pH of 4 is found in the stomach after food has been ingested, a pH of 6-7 is found in the upper intestine, and a pH of 8 is found in the lower intestine. R-(+)-α-Lipoate has both hydrophilic and lipophilic properties. Based on this combination properties, it is chemically reasonable to expect that R-(+)-α-lipoate binds to lipophilic membranes, as are found on cells throughout the body, and is taken up, at least in part, by absorption of magnesium-bound lipoate from the gastrointestinal tract. Thus, its bioavailability is unexpectedly high, as compared to conventional, water-insoluble magnesium salts.

A unit dose or serving of a composition of the invention provides from 5 mg to about 100 mg magnesium, on an elemental basis, and from 95 mg to about 1,900 mg of R-(+)-α-lipoate in the form of pharmaceutical quality magnesium R-(+)-alpha-lipoate. A clinician has the training and expertise to determine which dose level and related dosage regimen are most appropriate for a patient.

The compositions of this invention can be administered by any means that effects contact of the active ingredients with the site of action in the body of a warm-blooded animal. A most preferred means of administration is by the oral route (i.e., ingestion). The compositions of this invention can be administered one or more times each day, so as to facilitate and enhance compliance with dosage regimens.

The active ingredients can be administered by the oral route in solid dosage forms, such as tablets, capsules, and powders, or in liquid dosage forms, such as elixirs, syrups, and suspensions. The pharmaceutical composition is preferably made in the form of a dosage unit containing a particular amount of each active ingredient. One most preferred oral dosage form of a composition of the present invention is an admixture of powders contained within a sachet. Because a composition of the present invention is not hygroscopic and has no repugnant taste or odor, the admixture of powders comprising a composition of the present invention can be sprinkled on food or stirred into beverages to enhance ease of use and support high levels of compliance with daily dosage regimens.

In general, the pharmaceutical dosage forms of compositions of this invention can be prepared by conventional techniques, as are described in *Remington's Pharmaceutical Sciences*, a standard reference in this field [Gennaro A R, Ed. *Remington: The Science and Practice of Pharmacy*. 20$^{th}$ Edition. Baltimore: Lippincott, Williams & Williams, 2000]. For therapeutic purposes, the active components of this combination therapy invention are ordinarily combined with one or more adjuvants appropriate to the indicated route of administration. If administered per os, the components may be admixed with lactose, sucrose, starch powder, cellulose esters of alkanoic acids, cellulose alkyl esters, talc, stearic acid, magnesium stearate, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropyl methylcellulose. Solid dosage forms can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Both the solid and liquid oral dosage forms can contain coloring and flavoring to increase patient acceptance. Other adjuvants and modes of administration are well and widely known in the pharmaceutical art.

Dosing for oral administration may be with a regimen calling for single daily dose, or for a single dose every other day, or for multiple, spaced doses throughout the day. The active agents which make up the therapy may be administered simultaneously, either in a combined dosage form or in separate dosage forms intended for substantially simultaneous oral administration. The active agents which make up the therapy may also be administered sequentially, with either active component being administered by a regimen calling for two-step ingestion. Thus, a regimen may call for sequential administration of the active agents with spaced-apart ingestion of the separate, active agents. The time period between the multiple ingestion steps may range from a few minutes to several hours, depending upon the properties of each active agent such a potency, solubility, bioavailability, plasma half-life and kinetic profile of the agent, as well as depending upon the age and condition of the patient. The active agents of the therapy whether administered simultaneously, substantially simultaneously, or sequentially, may involve a regimen calling for administration of one active agent by oral route and the other active agent by intravenous route. Whether the active agents of the therapy are administered by oral or intravenous route, separately or together, each such active agent will be contained in a suitable pharmaceutical formulation of pharmaceutically-acceptable excipients, diluents or other formulations components.

EXAMPLE 1

Preparation and analysis of pharmaceutical quality magnesium R-(+)-alpha-lipoate A. Attempted methods of preparing magnesium R-(+)-alpha-lipoate. Seven different reactions were carried out repetitively in an attempt to prepare magnesium R-(+)-alpha-lipoate (Table 1). Each product was analyzed for magnesium content by titration with eriochrome black and for R-(+)-alpha-lipoate content by HPLC.

TABLE 1

Attempted methods of preparing magnesium R-(+)-alpha-lipoate

| Rx. | R-(+)-alpha-Lipoic Acid | Mg Reagent | Conditions | Result |
|---|---|---|---|---|
| A | R-(+)-α-lipoic acid; 2 equivalents dissolved in anhydrous ethanol | 1 equivalent of magnesium ethoxide in anhydrous ethanol | Reaction at room temperature | Evaporation of the solvent, as disclosed in U.S. Pat. No. 6,288,106, left a stringy, intractable polymeric gum that could not be dissolved in water, organic solvents, or acids. Analytical results indicated that the product was not magnesium R-(+)-alpha-lipoate. |
| B | R-(+)-α-lipoic acid; 2 equivalents dissolved in acetone | 1 equivalent of magnesium methoxide in anhydrous methanol | Reaction at room temperature | A green solid precipitated and was isolated by filtration. The solid could not be dissolved in water, organic solvents, or acids. Analytical results indicated that the product was not magnesium R-(+)-alpha-lipoate. |
| C | R-(+)-α-lipoic acid; 2 equivalents dissolved in methanol | 1 equivalent of magnesium methoxide in anhydrous methanol | Reaction at room temperature | No solid precipitated from the reaction. |
| D | R-(+)-α-lipoic acid; 2 equivalents dissolved in ethanol | 1 equivalent of magnesium methoxide in anhydrous methanol | Reaction at room temperature | No solid precipitated from the reaction |
| E | R-(+)-α-lipoic acid; 2 equivalents dissolved in acetonitrile | 1 equivalent of magnesium methoxide in anhydrous methanol | Reaction at room temperature | A mixture of green solid and yellow-green solid precipitated and was isolated by filtration. The solids did not completely dissolve in organic solvents or acids. Analytical results indicated that the product was not magnesium R-(+)-alpha-lipoate. |
| F | R-(+)-α-lipoic acid; 2 equivalents dissolved in isopropyl alcohol | 1 equivalent of magnesium t-butoxide in anhydrous ethanol/acetonitrile | Reaction at room temperature | A pale yellow solid precipitated and was isolated by filtration. The yield of product was about 50% of theoretical. Analytical results indicated that the product was magnesium R-(+)-alpha-lipoate. |
| G | R-(+)-α-lipoic acid; 2 equivalents dissolved in acetonitrile | 1 equivalent of magnesium acetylacetonate in anhydrous methanol | Reaction at room temperature | A pale yellow solid precipitated and was isolated by filtration. Analytical results indicated that the product was magnesium mono-R-(+)-alpha-lipoate mono-acetylacetonate. |

B. Method of preparation of pharmaceutical quality magnesium R-(+)-alpha-lipoate of this invention. Dropwise addition of 485 mL of a solution of magnesium methoxide in methanol (a volume equivalent to about one mole of magnesium methoxide) to a clear solution of about 100 g of R-(+)-alpha-lipoic acid (2 mole equivalents) having a chiral purity of about 96% in 3,500 mL of methanol-isopropyl alcohol solution maintained under an inert gas and shielded from light provided magnesium R-(+)-alpha-lipoate as a solid, pale yellow precipitate. Magnesium R-(+)-α-lipoate was isolated by filtration and purified from contaminants by washing with fresh isopropyl alcohol. Magnesium R-(+)-α-lipoate did not melt at temperatures below 300° C. Analysis for magnesium content by titration showed that the magnesium content was 5.6% by weight, as expected. Analysis for R-(+)-α-lipoate content by HPLC showed that the R-(+)-α-lipoate was 94.4% by weight, as expected. HPLC analysis by a method useful for the determination of chiral purity confirmed that the magnesium R-(+)-alpha-lipoate obtained therefrom had at least about 95% chiral purity; thus, no racemization occurred during its preparation. Analysis of trace metals by inductively coupled plasma mass spectrometry showed that magnesium R-(+)-α-lipoate contained only very low parts per million levels of toxic metals, such as aluminum, tin, arsenic, barium, lead, and thallium. Thus, pharmaceutical quality magnesium R-(+)-α-lipoate was obtained in greater than 65% yields and had greater than 95% purity and greater than 95% chiral purity.

EXAMPLE 2

Stability of magnesium R-(+)-alpha-lipoate of this invention.

Samples of the magnesium R-(+)-α-lipoate of Example 1.B. were stored at room temperature. Test samples of magnesium R-(+)-α-lipoate were exposed to ambient environments with relative humidities as high as 75% for a period of a week. The physical appearance and properties of the compound did not change during storage. The data indicated that the compound was not hygroscopic and was stable during storage under these conditions. Test samples of magnesium R-(+)-α-lipoate were stored at ambient temperatures for two years. The physical appearance and properties of the compound did not change. Magnesium R-(+)-α-lipoate was a light yellow powder throughout the storage period and showed no visible signs of polymerization or degradation. Chemical analyses indicated that its chemical composition, purity, and chiral purity did not change during storage under these conditions. In contrast, storage of R-(+)-α-lipoic acid under these conditions resulted in clumping of the compound, development of a strong sulfur odor, and formation of small and visible gummy balls of dark yellow material characteristic of polylipoate degradation products.

EXAMPLE 3

Bioavailability of magnesium R-(+)-alpha-lipoate of this invention.

The percentage of bioavailable magnesium was determined as the percentage of phosphorous bound from a solution of phosphate.

Materials. Materials other than magnesium R-(+)-α-lipoate were obtained from commercial suppliers (e.g., Sigma Aldrich Chemical Co., Inc., VWR, Alfa Aesar Chemical Co., Jost Chemical Co.).

Methods. The following procedure was employed. Experiments were completed in triplicate in which 1.43 g of $NaH_2PO_4 \cdot H_2O$ (329 mg of elemental phosphorus) was dissolved in 570 mL of deionized water. The test or control compound was dissolved in deionized water to a volume of 30 mL. The resulting solution was added to the phosphorus solution to give a final volume of 600 mL. For each study, the phosphorus solutions were titrated by addition of concentrated HCl or NaOH to five different initial pH levels: 4, 5, 6, 7, and 8. (These values of pH span the pH range of the gastrointestinal tract.) Then the beakers containing the solutions were covered with plastic wrap and placed in a shaker bath at 37° C., shaking at ~20 cycles per minute. This stirring rate has been selected because in vitro antacid activity at such low stirring rates has been reported to correlate well with in vivo antacid activity in the stomach. Samples for ion chromatographic assay of phosphate (Pi) were taken just before titrations to the initial pH and at 1, 4 and 10 h post-mixing; these later intervals have been reported to correspond to the approximate residence time in stomach, the time available for absorption in the small intestine, and the maximum time available for phosphorus binding that have been reported in related in vivo studies, respectively. The percentage decrease in phosphorus concentration from the original concentration in the phosphorus solution to that of the filtrate represents the bioavailable magnesium in magnesium R-(+)-α-lipoate (Mg RALA).

The experimental data (FIG. 1) demonstrate that the magnesium ion of magnesium R-(+)-α-lipoate is bioavailable in all parts of the gastrointestinal tract. Although magnesium R-(+)-α-lipoate has no significant solubility in this pH range, experimental data show that this magnesium salt dissociates sufficiently to provide 82% to 100% of the available magnesium throughout the pH range 4-8.

All mentioned references are incorporated by reference as if here written. When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

Without further elaboration, it is believed that one skilled in the art can, using the preceding description, utilize the present invention to its fullest extent. The specific embodiments are, therefore, to be construed as merely illustrative, and not limitative of the remainder of the disclosure in any way whatsoever.

I claim:

1. A method of preparing pharmaceutical quality magnesium R-(+)-alpha-lipoate having greater than 95% purity and greater than 95% chiral purity, comprising:
    (a) preparing a clear solution of about two mole equivalents of R-(+)-alpha-lipoic acid having a chiral purity of about 95±5% in methanol and isopropyl alcohol and maintaining the lipoic acid solution under an inert gas and subdued lighting;
    (b) adding dropwise a volume of a solution of magnesium methoxide in methanol corresponding to about one mole equivalent of magnesium methoxide to the lipoic acid solution, thus providing a slurry of magnesium R-(+)-alpha-lipoate solid in the solution; and
    (c) isolating the magnesium R-(+)-alpha-lipoate.

* * * * *